United States Patent [19]

May et al.

[11] 4,251,215
[45] Feb. 17, 1981

[54] PHOSPHONITRILIC FLUOROELASTOMER LINED DENTURE

[75] Inventors: Paul May, New Orleans; Luis R. Guerra, Metairie, both of La.

[73] Assignee: Gulf South Research Institute, Baton Rouge, La.

[21] Appl. No.: 73,692

[22] Filed: Sep. 10, 1979

[51] Int. Cl.³ ............................................. A61C 13/22
[52] U.S. Cl. .................................... 433/168; 106/35; 260/998.11; 264/17
[58] Field of Search ......................... 433/168; 106/35; 260/998.11; 264/16, 17

[56] References Cited

U.S. PATENT DOCUMENTS

| | | | |
|---|---|---|---|
| 1,917,902 | 7/1933 | Rowe. | |
| 2,457,114 | 12/1948 | Amenta | 18/55.1 |
| 2,899,712 | 8/1959 | Smith | 18/55.1 |
| 3,251,910 | 5/1966 | Barnhart | 264/17 |
| 3,589,010 | 6/1971 | Taniguchi | 32/2 |
| 3,628,988 | 12/1971 | Stol et al. | 264/16 |
| 3,826,002 | 7/1974 | Faust et al. | 32/2 |
| 3,886,659 | 6/1975 | Reifke | 32/2 |
| 3,889,374 | 6/1975 | Saffir | 32/2 |
| 3,970,533 | 7/1976 | Kyker et al. | 260/926 |
| 4,024,636 | 5/1977 | Colpitts et al. | 32/2 |

*Primary Examiner*—Lorenzo B. Hayes
*Attorney, Agent, or Firm*—Geoffrey L. Chase; Martin P. Hoffman

[57] ABSTRACT

A prosthetic denture which is lined on its tissue bearing surfaces with a phosphonitrilic fluoroelastomer layer to provide a resilient, durable cushion for the prosthetic denture; and a method for making same is disclosed.

10 Claims, 8 Drawing Figures

PHOSPHONITRILIC FLUOROELASTOMER LINED DENTURE

BACKGROUND OF THE INVENTION

1. Field of the Invention

This invention relates to liners for prosthetic dental fixtures and to a method for producing such fixtures.

Difficulties are frequently reported by the dental profession in the permanent fitting of dental fixtures to patients. These difficulties include the failure of the oral bone structure to retain its original form after removal of natural teeth and the sensitivity of the mouth tissue to the pressure contact of artificial dental fixtures. An additional difficulty involves the build up of tartar and plaque on the surfaces of such fixtures with the attendant adverse effects due to the uneven surface produced by such buildups. The retention of bacteria in such buildups also has adverse affects.

These problems have been addressed by those persons working in the dental prosthesis art. Various attempts have been made to construct dental fixture liners having the following characteristics: (1) insolubility in the mouth environment, (2) adhesion to the denture fixture base, (3) permanent softness and resiliency, (4) low water absorption, (5) insignificant dimensional change during liner fabrication, (6) ease of cleaning with abrasion resistance, (7) color stability, and (8) satisfactory tissue tolerance.

2. Prior Art

The prior art has attempted to provide a suitable solution to the problem of dental fixture fit and acceptability. Various soft and elastic materials have been proposed to be used as dental fixture liners, such as natural and silicone rubbers, highly plasticized polyvinylchloride, gutta percha, butylmethacrylate polymers, polymers of esters derived from methacrylic acid, acrylic acid and higher aliphatic alcohols, crosslinked polymers of glycol-acrylates, glycol-methacrylates, and polyurethanes. However, none of these materials have had satisfactory, long-term achievement of the above-listed criteria.

In U.S. Pat. No. 3,251,910, Barnhart, a silicone rubber denture liner is disclosed. U.S. Pat. No. 3,886,659, Reifke, teaches the use of a multi-pocketed denture liner of rubber or plastic. In U.S. Pat. No. 3,889,374, Saffir, a dental liner of methyl methacrylate resin is disposed on a fluorinated resin base. This patent teaches the use of organic backbone, fluorinated polymers only; and these are used as the base material with the specific attempt to avoid tissue bearing contact. U.S. Pat. No. 4,024,636, Colpitts, discloses a denture of hard polyurethane with a soft polyurethane liner. Other patents of general interest include U.S. Pat. Nos. 554,740, Spyer; 1,917,902, Rowe; 2,457,114, Amenta, 2,888,746, Levy; 2,899,712, Smith; 3,589,010, Taniguchi, 3,628,988, Stol; 3,826,002, Faust; and 4,050,156, Chasanoff.

SUMMARY OF THE INVENTION

With a view to overcoming the problems in the previously designed dental fixtures and with an awareness of the short-comings of the prior art attempts to solve those problems, it is the main objective of the subject invention to provide a dental fixture and method of making the same wherein a permanently lined dental fixture is fabricated from a soft, resilient layer of phosphonitrilic fluoroelastomer, bonded to a dental fixture base. The preferred elastomers are linear polymeric phosphonitrilic fluoroelastomers which are often referred to as polyphosphazenes.

Another objective is to produce a fixture having a liner which is inert to the environment of the human mouth.

Yet another objective is to produce such a dental fixture having a liner which can be adhesively bonded to said dental fixture.

Finally, it is an objective to provide a lined dental fixture wherein the lining is pigmented to provide a flesh-tone similar to the dental fixture.

BRIEF DESCRIPTION OF THE DRAWINGS

The invention will be more fully described by reference to the embodiments disclosed in the accompanying drawings.

DETAILED DESCRIPTION OF PREFERRED EMBODIMENT

Figure 1:
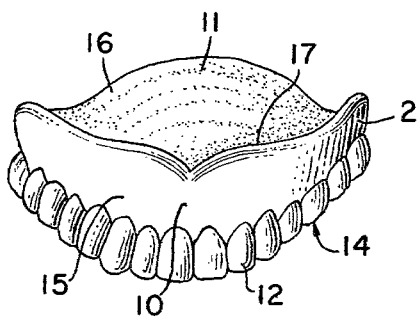
FIG. 1 is a perspective view of an upper denture of the subject invention.
Figure 2:
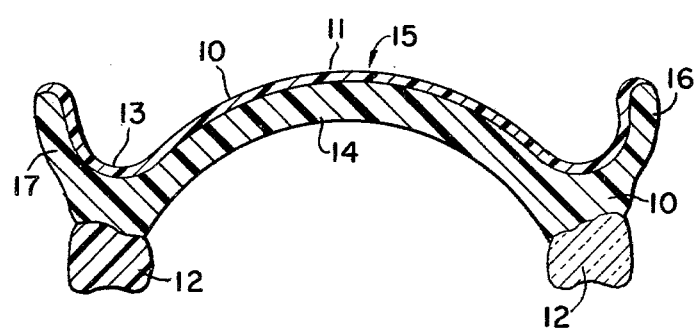
FIG. 2 is a sectional view of the denture of FIG. 1 taken along the line 2—2.

Referring to FIGS. 1-2, a prosthetic denture is shown having a denture base 10 which is molded to simulate the upper dental structure of the human mouth. The denture base 10 has a set of artificial porcelain or plastic teeth 12 affixed to said base by any of the conventional means of fitting or bonding such teeth to a denture such as taught in U.S. Pat. No. 2,457,114, U.S. Pat. No. 2,899,712 or U.S. Pat. No. 4,024,636.

A dental liner 11 consisting of a layer of phosphonitrilic fluoroelastomer is bonded to the tissue bearing surface 13 of the denture. By use of the phrase "tissue bearing surface," it is meant to denote that part of a denture which provides pressure contact of the denture against the gums and jawbone, as well as the palate, of the wearer. This surface 13 is distinguished from the non-pressure bearing surfaces of the denture, which contact the side or lips of the wearer's mouth.

The liner 11 covers those areas of the denture base which perform this pressure bearing function, as shown in FIG. 2. The liner is designed as a resilient, biocompatible, inert surface which cushions the action of the denture during its use, so as to provide comfort to the gums and the other tissue bearing surfaces 13.

Figure 3:
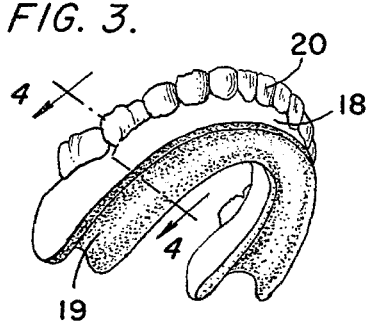
FIG. 3 is a perspective view of a lower denture of the subject invention.
Figure 4:
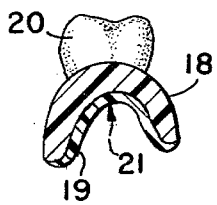
FIG. 4 is a sectional view of the denture of FIG. 3 taken along the line 4—4.

A corresponding liner structure is depicted in FIGS. 3-4. A lower denture is shown in FIG. 3 having a base 18. Artificial teeth 20 of porcelain or plastic are mounted in this base 18 in a similar manner as described for the upper denture. Such mountings include mechanical linkage or adhesive securement of said teeth to the denture base 18. The denture base 18 has a liner 19 bonded to the tissue bearing surface 21 of the base. The liner consists of a 1-3 mm layer of a phosphonitrilic fluoroelastomer.

The above-described lined denture provides a prosthetic dental fixture which has the same natural appearance of prior art dentures, but additionally, it provides a resilient cushioned layer on the tissue bearing surfaces of the denture. Such a liner is beneficial to counteract the effects of senile atrophy or hypersensitivity of the gum tissues due to infection or irradiation.

The polymers used in the liner of the subject invention also provide the previously mentioned characteristics of a good dental liner including lower water absorption, permanent resilience, inertness and ease of cleaning especially for containment of tartar and plaque development, as well as satisfactory biocompatibility. These phosphonitrilic fluoroelastomers, called polyphosphazenes, are prepared by thermal polymerization of cyclic trimers as follows:

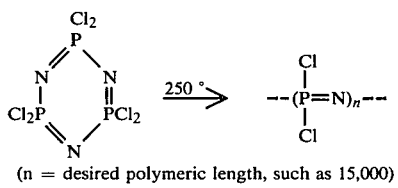

(n = desired polymeric length, such as 15,000)

The resultant poly(dichlorophosphazene) has undesirable characteristics. Therefore, the chloride is replaced with organic radicals, such as fluorocarbon radicals, as follows:

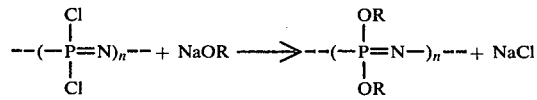

The preferred form of such an organic radical derived linear phosphonitrilic polymer is a polyphosphonitrilic fluoroelastomer having the following unit structure:

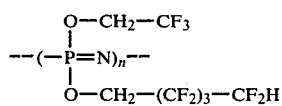

TABLE 1

COMPARATIVE PHYSICAL DATA OF AN IDEAL LINER AND A POLYPHOSPHAZENE (PNF-200)

|  | 100% Modulus (psi) | Tensile Strength (psi) | Ultimate Elongation (%) | Shore A Hardness |
|---|---|---|---|---|
| Ideal Liner Material | <200 | >1000 | >300 | <40 |
| PNF-200 (Firestone) | 200 | 1000 | 300 | 30 → 40 |

Despite the fact that the phosphonitrilic fluoroelastomer liners are bonded to the denture base at a position where visibility is negligible in use, the elastomers can contain flesh-coloring material to provide an overall acceptable appearance for the wearer. Coloring is imparted at the time of the fabrication of the basic sheet stock from which the liner is cut and formed. The particular pigments can be chosen from any F.D.A. approved pigmenting agents, such as $Fe_2O_3$ or $TiO_2$.

The phosphonitrilic fluoroelastomer (polyphosphazene) lined denture is prepared, preferably, by the following method.

A commercially available polyphosphazene is mixed with an F.D.A. approved pigment and 1% benzoyl peroxide at room temperature. The batch can be mixed in a 2-roll mill and cast in a suitable layer having a thickness in the range of 1-3 mm and preferably 2 mm. The cast polymer sheet is heated to 105° C. for one hour to crosslink the polymer. Optionally, the crosslinking can be achieved by irradiation of the cast polymer. The cured elastomers have a density of 1.75 and exhibit the necessary properties for a suitable denture liner.

A stone model of the denture recipient's gum and jaw structure is then formed in a separate operation. This can be performed by a standard technique in which a temporary negative cast is made in the recipient's mouth and a permanent positive stone model is then made from the negative cast.

The stone model is then used to preform the denture liner. The polyphosphazene cast sheet is first pretreated on its denture contacting side to create polar groups on its surface by treating the surface with: (a) acidic agents, such as sulfuric acid, chlorosulfuric acid or $SO_3$/triethylphosphate; or (b) oxidizing agents, such as peracetic acid and perfluoroperacetic acid. These polar groups (sulfonic or hydroxyl, respectively) enhance the adhesion of the polyphosphazene liner to the denture base during molding. Alternately, the liner can be bonded to the base by an adhesive, such as acrylic, epoxy, anhydrides or urethane adhesive resins. In this case, pretreatment of the liner surface would not be necessary. Adhesive would be applied to the denture contacting side of the liner after vacuum forming and prior to molding of the liner to the uncured acrylic denture base.

Figure 5:
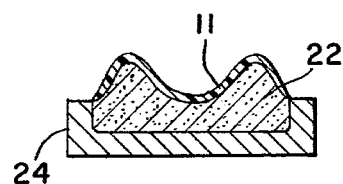
FIG. 5 is a sectional view of the upper half of a mold flask for forming the liner of the subject invention.

A section of the cast polyphosphazene cured sheet is cut in the desired shape of the denture. The cut sheet section is then heated to provide a soft pliable consistency to the section, but not so much as to create further crosslinking. The sheet section is then vacuum formed over the appropriate surface of the stone model, cooled to room temperature and removed. See FIG. 5.

Figure 6:
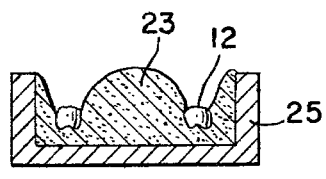
FIG. 6 is a sectional view of the lower half of a mold flask for forming a denture of the subject invention.
Figure 7:
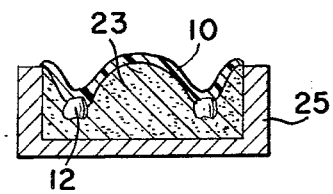
FIG. 7 is a sectional view of the lower half of a mold flask with denture material therein.

Referring to FIGS. 5-8, the stone model 22, is then placed in the mold flask 24 and the liner is placed over said model. The other half of the model 23 is placed in its respective half of the flask 25 and polymethylmethacrylate resin denture base material 10 is packed in the flask 25 over an appropriate set of porcelain or plastic artificial teeth 12 (FIGS. 6-7).

Figure 8:
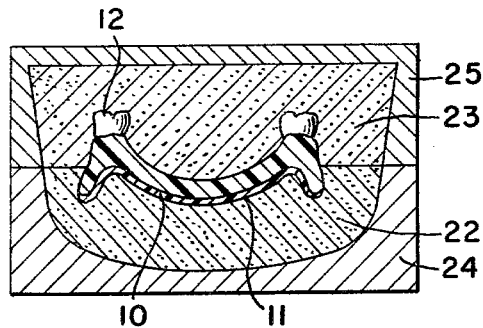
FIG. 8 is a sectional view of the mated halves of a mold flask with the composite denture of the subject invention.

The stone model and flask halves are then closed and the composite denture is heat cured at sufficient time and temperature to cure the particular acrylic resin used as a base material (FIG. 8). The cured, lined denture is then cooled and removed from the flask for final finishing. The finishing can include removal of flashing and spot filing of any rough points on the denture.

This method can be used to form the lower denture in the same manner as described for the fabrication of the upper denture. In addition, other prosthetic dental fixtures can be fabricated by the method of the subject invention, such as plates and bridges.

Whereas the invention is described with particular reference to the preferred article and method, it is to be understood that obvious modifications and equivalents will be apparent to one skilled in the art and such modifications and equivalents are deemed to be within the scope of the invention which is defined by the claims as follows.

We claim:

1. A prosthetic dental fixture comprising a biocompatible cushioning liner of a linear phosphonitrilic fluoroelastomer, having the general formula

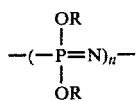

wherein R is a fluorocarbon, bonded to the tissue bearing surfaces of the base of said prosthetic dental fixture.

2. The invention of claim 1 wherein the linear phosphonitrilic fluoroelastomer liner contains suitable pigments for coloration of said liner to match the dental fixture base.

3. The invention of claim 2 wherein the pigments are selected from the group comprising iron oxide and titanium dioxide.

4. The invention of claim 1 wherein the phosphonitrilic fluoroelastomer liner is bonded to the tissue bearing surfaces of the prosthetic dental fixture base by a suitable adhesive selected from the group comprising acrylic resins, epoxy resins, and urethane resins.

5. The invention of claim 1 wherein the dental fixture base consists of polymethylmethacrylate.

6. The invention of claim 1 wherein the phosphonitrilic fluoroelastomer liner is pretreated on its denture base contacting surface to provide adherence enhancing polar chemical groups thereon to facilitate liner to dental base bonding.

7. The invention of claim 1 wherein the phosphonitrilic fluoroelastomer liner is pretreated on its denture base contacting surface to provide adherence enhancing hydroxyl chemical groups thereon to facilitate liner to dental base bonding.

8. The invention of claim 1 wherein the phosphonitrilic fluoroelastomer has a modulus of 200 psi, a tensile strength of 1000 psi, an ultimate elongation of 300% and a Shore A hardness of 30 to 40.

9. A polymethylmethacrylate prosthetic denture having a biocompatible, hydrophobic, resilient, cushioning denture liner consisting of a linear phosphonitrilic fluoroelastomer, having the general formula

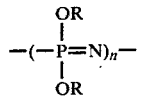

wherein R is a fluorocarbon, bonded to the tissue bearing surfaces of the base of said denture; said liner consisting of a 1–3 mm layer adhesively bonded to said base by an adhesive.

10. A method for making a lined denture wherein the lining is fabricated of a phosphonitrilic fluoroelastomer having the general formula

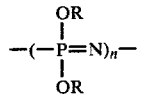

wherein R is a fluorocarbon, comprising the steps of:
(a) constructing a stone model from a dental fixture recipient;
(b) heat forming a sheet of phosphonitrilic fluoroelastomer on said stone model;
(c) placing said formed sheet and stone model in a mold flask;
(d) packing said flask with an uncured acrylic denture base material;
(e) closing said flask and heat curing the denture base and said liner to bond the composite; and
(f) removing the lined denture base and finishing same.

* * * * *